United States Patent [19]
Wolk

[11] Patent Number: 5,820,368
[45] Date of Patent: Oct. 13, 1998

[54] DISPOSABLE APPLICATOR FOR FORMING AND RETAINING AN ORTHODONTIC ATTACHMENT

[76] Inventor: Roger S. Wolk, 28 Malibu Colony, Malibu, Calif. 90265

[21] Appl. No.: 600,040

[22] Filed: Feb. 12, 1996

Related U.S. Application Data

[63] Continuation-in-part of Ser. No. 546,602, Oct. 23, 1995, Pat. No. 5,681,163.

[51] Int. Cl.$^6$ ..................................................... A61C 7/00
[52] U.S. Cl. .............................................. 433/3; 433/141
[58] Field of Search .................................. 433/3, 4, 141, 433/163, 164

[56] References Cited

U.S. PATENT DOCUMENTS

| | | | |
|---|---|---|---|
| 1,676,715 | 7/1928 | Snyder | 433/164 |
| 4,375,961 | 3/1983 | Brooks | 433/159 |
| 4,904,183 | 2/1990 | Hannan et al. | 433/3 |
| 5,242,302 | 9/1993 | Riehm | 433/164 |
| 5,358,404 | 10/1994 | Schumacher | 433/164 |

*Primary Examiner*—Cary E. O'Connor
*Attorney, Agent, or Firm*—Thomas I. Rozsa; Tony D. Chen

[57] ABSTRACT

A disposable applicator has a translucent bonder tip member that forms an orthodontic attachment which bonds to the surface of the tooth in one easy motion, where an orthodontic wire or rubber band may be placed thereon and held in position to correct irregular teeth of an individual. The curing resin is placed in a shaped contour cavity of the bonder tip member and then it is positioned against each surface of the tooth. Then a curing light is shined on the resin through the translucent bonder tip member so that the resin becomes hardened and forms the orthodontic attachment on the surface of the tooth. The disposable applicator may also retain a conventional orthodontic button therein so that an orthodontist can rapidly and effortlessly bond the orthodontic button to each surface of the tooth.

33 Claims, 3 Drawing Sheets

DISPOSABLE APPLICATOR FOR FORMING AND RETAINING AN ORTHODONTIC ATTACHMENT

This application is a Continuation-In-Part of the patent application Ser. No. 08/546,602 filed on Oct. 23, 1995, now U.S. Pat. No. 5,681,163.

BACKGROUND OF THE INVENTION

1. Field of the Invention

The present invention generally relates to the field of dentistry. More particularly, the present invention relates to the field of orthodontics for applying a small, precise mound of curing resin to bond a lingual or labial retainer to teeth of a patient. In particular, the present invention relates to the field of forming an orthodontic bracket on the surfaces of teeth and for forming and retaining an orthodontic button in an applicator so that the button can be bonded to the surfaces of teeth.

2. Description of the Prior Art

Presently, labial and lingual retainers are bonded to surfaces of teeth by using an applicator such as a tiny dental tool. The disadvantage in using the dental tool is that a precise amount and shape or contour for the curing resin has to be applied for bonding an orthodontic wire to the surface of each tooth. At times, the orthodontist may apply too much curing resin to bond the orthodontic wire to the surface of each tooth or does not apply enough curing resin to the orthodontic wire to keep the wire securely over each tooth. This process is time consuming and it is sloppy to apply the resin with the conventional dental tool.

Therefore, it is highly desirable to have a very efficient and also very effective design and construction of a disposable resin applicator for assisting an orthodontist to apply a small, precise mound of resin to hold the orthodontic wire to the teeth of a patient. It is also desirable to provide a disposable resin applicator with the capability of rapidly and effortless applying a neat mound of adhesive resin on each surface of the tooth for holding the orthodontic wire in place.

In addition, the orthodontist utilizes conventional orthodontic bonded parts, e.g., brackets and buttons. The orthodontic brackets are bonded to the surfaces of teeth for holding an orthodontic wire thereon to correct irregular teeth of an individual. The orthodontic buttons are bonded to the surfaces of teeth for holding a rubber band around the button in order to adjust the teeth. Presently, prior art conventional orthodontic attachments are mass produced by manufacturers. These orthodontic attachments are very small and difficult to handle by the orthodontist's hands, and therefore requires a dental tool such as tweezers for picking up and holding the small orthodontic attachment to the surface of the tooth to be bonded. The disadvantage with this procedure is that the orthodontic attachments are expensive and difficult to handle and sometimes are inadvertently dropped during a procedure. Another disadvantage is that tweezers require a slight inward pressure on both of the legs to hold the orthodontic attachment in position and therefore it is not always possible to maintain the orthodontic attachment in position, and thereby the orthodontic attachment may become loosened from the tweezers and lost.

Therefore, it is highly desirable to have a very efficient and effective design and construction of a disposable applicator for forming a specialized unique small orthodontic bracket on the surface of each tooth so that an orthodontic wire may be placed thereon and held in place to correct irregular teeth of an individual. It is also desirable to provide a disposable applicator with the capability of rapidly forming a custom button and retaining a conventional orthodontic button therein so that an orthodontist can easily bond the orthodontic buttons to the surfaces of teeth or easily make his or her own custom orthodontic button.

SUMMARY OF THE INVENTION

The present invention is a novel and unique disposable resin applicator for applying a small, precise mound of resin to hold an orthodontic wire to the teeth of a patient. The disposable resin applicator assists an orthodontist to bond curing resin to the teeth to retain the wire used to stabilize the teeth after or during orthodontic movement.

The objective is to have a translucent wire bonder tip member which has two opposite wire slots through which the orthodontic wire can be inserted therein. An alignment guide runs approximately the length of the wire bonder tip member on either side so that it is easy to visually view where the wire slots are to be placed on the orthodontic wire. The curing resin is placed in a tiny cup on the wire bonder tip member and then it is placed over the orthodontic wire on the tooth so that the wire fits in the two wire slots so that the wire bonder tip member can be held by any means such as a tool. Then curing light is shined on the resin through the translucent wire bonder tip member so that the resin becomes hardened and holds the orthodontic wire to teeth.

Alternatively, in the event self curing resin is used instead of resin that requires a curing light, then it is not necessary for the wire bonder tip to be translucent. Accordingly, it is an object of the present invention to have a non translucent wire bonder tip member which has two opposite wire slots through which the orthodontic wire can be inserted therein. An alignment guide runs approximately the length of the wire bonder tip member on either side so that it is easy to visually view where the wire slots are to be placed on the orthodontic wire. The self curing resin is placed in a tiny cup on the wire bonder tip member and then it is placed over the orthodontic wire on the tooth so that the wire fits in the two wire slots so that the wire bonder tip member can be held by any means such as a tool. The wire bonder tip is then held in place until the self curing resin hardens thereby holding the orthodontic wire to the teeth.

It has been discovered, according to the present invention, that by providing a disposable resin applicator, it can be disposed of after use for preventing infectious diseases to other patients.

It has also been discovered, according to the present invention, that by providing a wire bonder tip member which has a tiny receptacle and two opposite wire slots on the periphery rim surrounding the receptacle through which an orthodontic wire can be inserted, it will consistently provide a small, precise mound of resin to hold the lingual or the labial wires to the teeth of a patient and thereby eliminate the guesswork in deciding the amount of resin to be applied.

It has additionally been discovered, according to the present invention, that by providing a wire bonder tip member with alignment guides on either side of the wire bonder tip member and aligned with the wire slots, it will provide an easy way to visually view where the wire slots are to be placed on the orthodontic wire.

It has further been discovered, according to the present invention, that by providing a translucent wire bonder tip member, it will provide an easy way for curing light to shine on the resin through the translucent wire bonder tip member so that the resin becomes hardened and holds the orthodontic wire to teeth.

It is therefore an object of the present invention to provide a disposable resin applicator so that when the resin applicator is used once, it can be disposed and thereby prevent the transmission of infectious diseases to other patients.

It is also an object of the present invention to provide a wire bonder tip member which comprises a tiny receptacle and two opposite wire slots, where an orthodontic wire can be inserted within the opposite wire slots, so that the receptacle can consistently provide a small, precise mound of resin to hold the lingual or the labial wires to the teeth of a patient without requiring guesswork as to the amount of resin to be applied.

It is an additional object of the present invention to provide a wire bonder tip member with alignment guides on either side of the wire bonder tip member and aligned with the wire slots, so that they provide an easy way to visually view where the wire slots are to be placed on the wire.

It is a further object of the present invention to provide a translucent wire bonder tip member, so that curing light can shine on the resin through the translucent wire bonder tip member and the resin becomes hardened and holds the orthodontic wire to teeth.

It is another object of the present invention to provide a wire bonder tip member that can be utilized with any common tool in the field of orthodontics such as forceps or other simple tools for holding the wire bonder tip member and applying the resin to the orthodontic wire and the teeth.

The present invention is also a disposable applicator for forming a small custom orthodontic bracket to surfaces of teeth so that an orthodontic wire may be placed thereon and held in position to correct irregular teeth of an individual. The orthodontic wire may also be used to stabilize the teeth after or during orthodontic movement.

The present invention can also be utilized as a disposable applicator for forming a small custom orthodontic button or to retain a conventional orthodontic button therein to be bonded to the surfaces of teeth.

The objective is to have a translucent bonder tip member for forming a custom orthodontic bracket to surfaces of teeth. The curing resin is placed in a shaped cavity on the bonder tip member and then it is placed on the surface of each tooth. Then a curing light is shined on the resin through the translucent bonder tip member so that the resin becomes hardened and forms the orthodontic bracket on the surface of the tooth.

It is still another object of the present invention to provide a disposable applicator for forming a custom orthodontic bracket which bonds to the surface of the tooth in one easy motion, thereby eliminating the need for conventional orthodontic brackets in some cases.

It is an additional object of the present invention to provide a disposable applicator for forming a custom orthodontic bracket which bonds to the surface of the tooth, where an orthodontic wire may be positioned thereon or an elastic band may be wrapped around the bracket and held in place to correct irregular teeth of an individual.

It is a further object of the present invention to provide a disposable applicator for forming a custom orthodontic button therein so that an orthodontist can rapidly and effortlessly make and bond an orthodontic button to the surface of each tooth.

It is an additional object of the present invention to provide a disposable applicator for retaining a conventional orthodontic button therein so that an orthodontist can rapidly and effortlessly bond the orthodontic button to the surface of each tooth.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DESCRIPTION OF THE PREFERRED EMBODIMENT

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
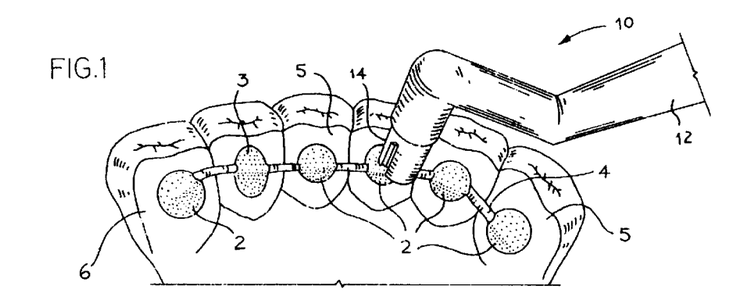
FIG. 1 is an illustration, showing the present invention disposable resin applicator applying the curing resin to surfaces of teeth for bonding an orthodontic wire thereon.

Referring to FIG. 1, there is illustrated at 10 the present invention disposable resin applicator for applying curing resin 2 to surfaces 5 of teeth 6 for bonding and holding an orthodontic wire 4 in place. The general description of the present invention disposable resin applicator will be focused on lingual wires, however, it will be appreciated that the present invention disposable resin applicator 10 can be utilized for labial wires as well.

Figures 2, 3, 4:
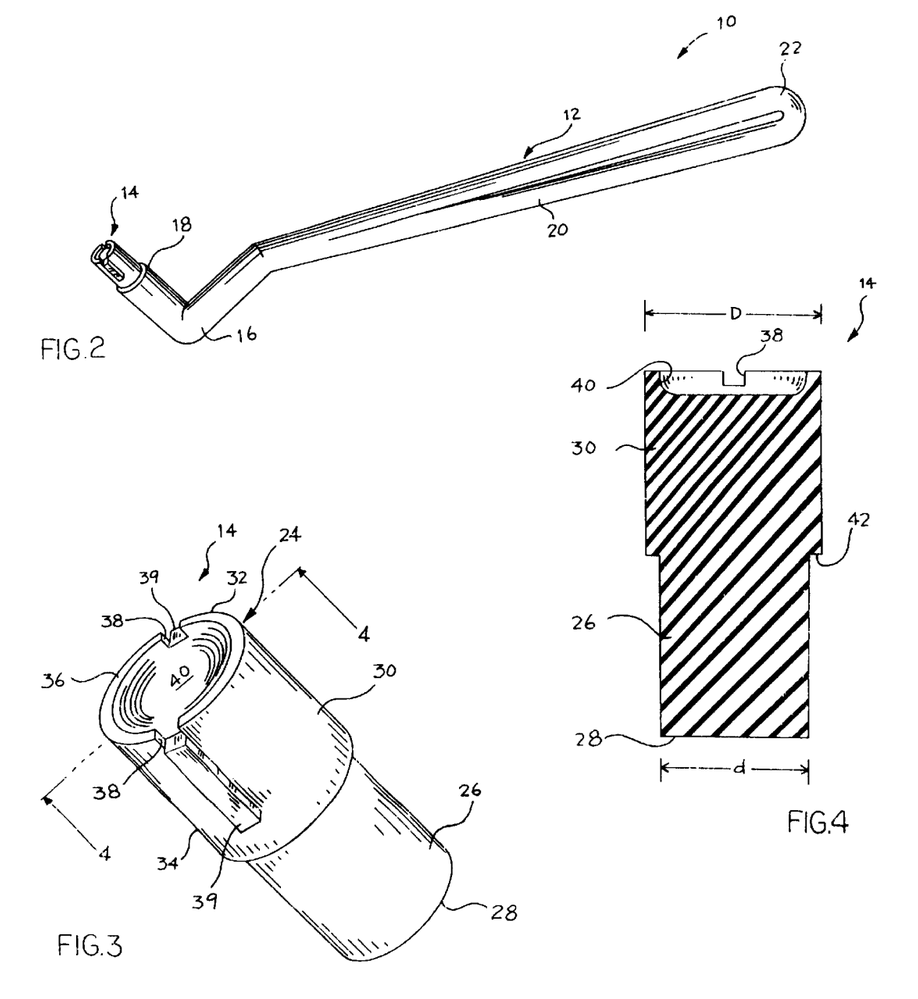
FIG. 2 is a perspective view of the preferred embodiment of the present invention disposable resin applicator.
FIG. 3 is an enlarged perspective view of the wire bonder tip member of the present invention disposable resin applicator.
FIG. 4 is an enlarged cross-sectional view taken along line 4—4 of FIG. 3.

Referring to FIG. 2, there is shown at 10 a perspective view of the present invention, a disposable resin applicator, which comprises an elongated dental tool member 12 and a translucent wire bonder tip member 14.

The tool member 12 has a proximal section 16 with a proximal end 18 and a distal section 20 with a distal end 22. The proximal section 16 of the tool member 12 is designed at an angle to fit within the mouth of a patient (see FIG. 1). The proximal end 18 of the tool member 12 has an opening therein for retaining the wire bonder tip member 14. The distal section 20 of the tool member 14 is shaped as a handle for grasping the tool member 14 by the orthodontist.

It will be appreciated that the dental tool member 12 is not limited to the figures as illustrated. It is emphasized that while the tool member 12 illustrated in the figures is preferred, it is also within the spirit and scope of the present invention to utilize forceps or other simple tools for retaining the wire bonder tip member 14.

Referring to FIG. 3, there is shown at 14 a perspective view the wire bonder tip member of the present invention. The wire bonder tip member 14 has a generally cylindrical shaped body 24. The cylindrical body 24 has a proximal section 26 with a proximal end 28, a distal section 30 with a distal end 32 and a circumferential sidewall 34. The distal end 32 of the body 24 has a periphery rim 36, two opposite wire slots or notches 38 located on the periphery rim 36 and a receptacle or tiny cup 40 therein surrounded by the periphery rim 36.

The wire bonder tip member 14 comprises an alignment guide member or a raised rib 39 (only one is shown) which runs along the length of the body 24 on either side and located on the distal section 30. The two alignment guide members 39 are respectively aligned with the two opposite slots 38 on the periphery rim 36 of the wire bonder tip member 14 to provide the orthodontist with a visual view as to where the two opposite slots 38 are located when the distal end 32 of the cylindrical body 24 abuts against the tooth 5 as shown in FIG. 1. The wire bonder tip member 14 is a tiny translucent "cookie cutter" with built-in wire slots 38 so that the curing light can shine on the resin through the translucent body 24 such that the resin becomes hardened and holds the orthodontic wire to the surfaces of the teeth.

Alternatively, it is not necessary that the type of curing resin used be resin that requires a curing light. It is possible to also use self curing resin which simply can be held in place during the hardening process. When using self curing resin, the wire bonded tip member 14 does not have to be translucent since it is not required to have any curing light shine through it. Through use of the self curing resin, the process is the same as just described except that no curing light is required and the wire bonder tip member is simply held in place while the self curing resin hardens.

Referring to FIG. 4, there is shown at 14 a cross-sectional view of the wire bonder tip member of the present invention. From this view, the diameter "D" of the distal section 30 is greater than the diameter "d" of the proximal section 26, where an edge 42 is formed so that when the wire bonder tip member 14 is press fitted within the opening at the proximal end 18 of the tool member 12, the edge 42 rests on the rim of the of the proximal end 18 (see FIG. 2).

Dimensions of the wire bonded to the teeth can vary. By way of example, the wire usually can have a diameter in the range of $14/1000$ to $20/1000$ of an inch. The receptacle 40 has a depth of $40/1000$ of an inch (1 mm) and the depth of the two opposite slots 38 to accommodate the orthodontic wire is $30/1000$ of an inch so that there is sufficient additional depth of resin material to form around and above the wire to be bonded. The diameter of the receptacle 40 is typically approximate 3½ millimeters or $140/1000$ of an inch. It will be appreciated that the dimensions described above are merely one illustrative embodiment and can include many other comparable sets of dimensions.

Referring to FIGS. 1 through 3, the present invention disposable resin applicator 10 is ideal for bonding a wire retainer after the first phase or the full phase treatment, where the wire is bonded on the lingual or the labial of the incisors of the patient. If the bond comes loose, it can be removed and remade in seconds without removing the entire wire from the other teeth.

The present invention disposable resin applicator 10 is used for applying a small, precise mound of resin to each surface of the tooth to hold an orthodontic wire in place. Essentially the technique is to have the disposable resin applicator 10 that assists the orthodontist to bond curing resin to the back or front surfaces of a tooth to retain an orthodontic wire during or after orthodontic treatment. The resin does not have to necessarily be of the oval shape 3 but can be circular 2, oval or any other shape (see FIG. 1).

The unique feature of the disposable resin applicator 10 is that it consistently forms a predetermined shape every time. The curing resin is placed in the tiny cup 40 and then it is placed over the orthodontic wire 4 behind the tooth so that the wire fits in the two opposite slots 38 so that the wire bonder tip member 14 can be held by any means such as a forceps tool. Then curing light is shined on the resin through the translucent wire bonder tip member 14 so that the resin becomes hardened and holds the orthodontic wire on the surfaces of the teeth. Also, the present invention can apply self curing resin that does not require the use of a curing light to harden the resin on the orthodontic wire and to the surfaces of the teeth.

The disposable resin applicator 10 may include means for retaining a wire to the back surfaces of teeth by providing means for retaining the curing resin during the time it is bonded with a curing light. The disposable resin applicator 10 may further have means for accommodating the orthodontic wire so that curing resin can be formed over the orthodontic wire as well as having the resin against the back surface of the teeth. The disposable resin applicator 10 may also be used to bond a wire to the surfaces of the teeth to move teeth.

The operation of the foregoing embodiment now will be described. First, the receptacle 40 is filled with the curing resin. Secondly, the receptacle 40 is placed on the tooth over the orthodontic wire, where the wire is positioned within the two opposite slots 38 and held in a desired location on the surface of the tooth while curing the resin, and thereby a bonded orthodontic wire with a small, precise mound of resin holding the orthodontic wire to the teeth of a patient is produced.

The cylindrical shaped body 24 of the wire bond tip member 14 can be made from several materials. The manufacturing process which could accommodate the construction of the wire bonder tip member 14 can be injection, etc. or other molding process. By way of example, the cylindrical shaped body 24 can be made of synthetic rubber or other suitable material.

The present invention conforms to conventional forms of manufacture or any other conventional way known to one-skilled in the art. In addition, the cylindrical shaped body 24 may be transparent so that curing light can shine on the resin through the wire bonder tip member 14 to harden the resin or the cylindrical shaped body 24 may not be transparent, and thereby a self curing resin is utilized that does not require a curing light.

The present invention has many advantageous features including: (a) the wire bonder tip member is disposable; (b) a small, precise mound of resin is formed consistently to hold the wire to the teeth; and (c) a predetermined shape of the resin is always formed.

Referring to FIGS. 5 through 9, there is shown another embodiment of the present invention disposable applicator. The disposable applicator comprises an elongated dental tool member which is identical to the one shown in FIG. 2, and the description of the dental tool member will not be repeated, and a translucent bonder tip member 114. The translucent bonder tip member 114 is installed in the dental tool member exactly the same as shown in FIGS. 1 and 2.

Figure 5:
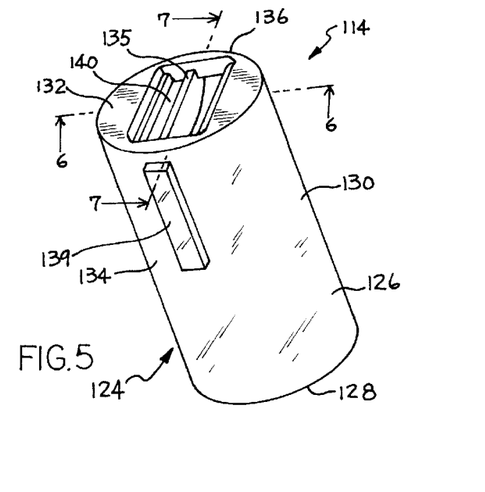
FIG. 5 is a perspective view of another embodiment of the present invention disposable applicator for forming a small custom orthodontic bracket to surfaces of teeth to retain an orthodontic wire thereon.
Figure 8:
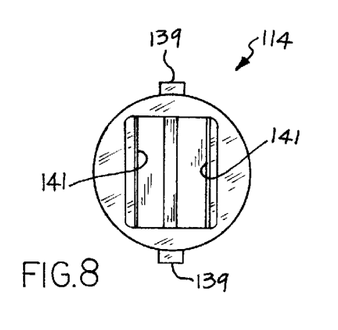
FIG. 8 is a top plan view of the present invention shown in FIG. 5.

Referring to FIGS. 5 and 8, there is shown at 114 the translucent bonder tip member of the present invention. The bonder tip member 114 is utilized for forming a custom orthodontic bracket to surfaces of teeth (see FIG. 10). The bonder tip member 114 has a generally cylindrical or ovoid or rectangular shaped body 124 which has a proximal section 126 with a proximal end 128, a distal section 130 with a distal end 132, and a circumferential sidewall 134. The distal end 132 of the bonder tip member 114 has a periphery rim 136 and a receptacle or a generally rectangular shaped contour cavity 140 therein surrounded by the periphery rim 136.

Figure 6:
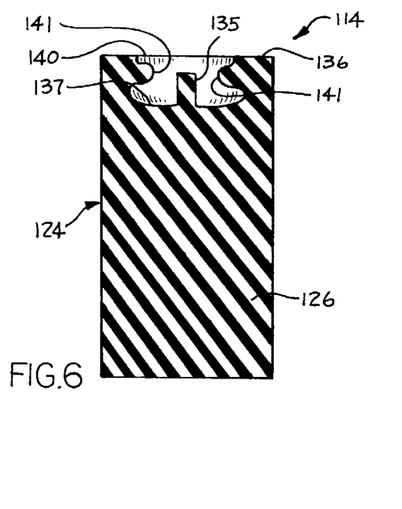
FIG. 6 is a cross-sectional view taken along line 6—6 of FIG. 5.
Figure 7:
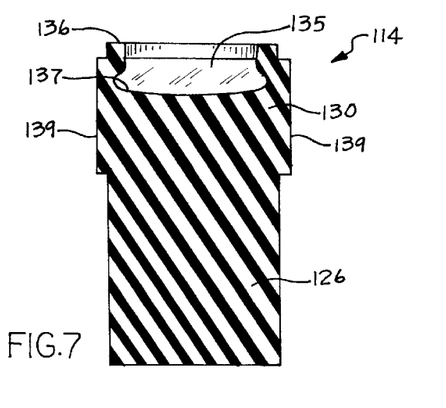
FIG. 7 is a cross-sectional view taken along line 7—7 of FIG. 5.

Referring to FIGS. 6 and 7, there are shown respective cross-sectional views of the bonder tip member 114. A raised ridge 135 is integrally formed on a bottom 137 of the rectangular shaped contour cavity 140 and extends upwardly just below the periphery rim 136 of the cylindrical shaped body 124. The raised ridge 135 forms the slot in the resin bracket bonded to the teeth (see FIG. 10). This slot is utilized for retaining an orthodontic wire therein. Two opposite protruding columns 141 are integrally formed with the side interior of the rectangular shaped contour cavity 140, where the raised ridge 135 is located between the protruding columns 141. These protruding columns 141 form the pedestal of the orthodontic bracket 147 which is shown from top to bottom (see FIG. 10). A rubber band or an elastomeric or wire ligature may be wrapped around the orthodontic bracket and held in position by the pedestal formed from the two opposite protruding columns 141. The function of the rubber band, the elastomeric or the wire ligature is to hold the orthodontic wire into the slot.

By way of example, the orthodontic wire usually can have a diameter approximately $20/1000$ of an inch. The shaped contour cavity 140 has a depth of $100/1000$ of an inch and the raised ridge which forms the slot has a height of approximately $40/1000$ of an inch to accommodate the orthodontic wire. It will be appreciated that the dimensions described above are merely one illustrative embodiment and can include many other comparable sets of dimensions.

The bonder tip member 114 also has one or two guide members or ribs 139 running in line with the raised ridge 135 along a partial length of the body 124 on either side and located on the distal section 130. The guide members 139 provide a visual aid for the orthodontist to configure the slot on the orthodontic bracket.

It will be appreciated that the rectangular shaped contour cavity 140 is not limited to the structure just described above. It is emphasized that while the rectangular shaped contour cavity 140 is preferred, it is also within the spirit and scope of the present invention to have a multiplicity of shaped contour cavities, for example, a negative-mold shaped which is to an anvil, a flat head portion of a screw or any other suitable shapes. In addition, it will not be too difficult for one skilled in the art to have a different shape negative-mold structure created by the bonder tip member 114.

The bonder tip member 114 is a tiny translucent device such that the curing light can shine on the resin through the translucent body 124 so that the resin becomes hardened and forms a small orthodontic bracket to the surfaces of the teeth. Alternatively, it is not necessary that the type of curing resin utilized be resin that requires a curing light.

It is also possible to utilize self curing resin which simply can be held in place during the hardening process. When using self curing resin, the bonded tip member 114 does not have to be translucent since it is not required to have any curing light shine through it. Through use of the self curing resin, the process is the same as described above except that no curing light is required and the bonder tip member 114 is simply held in position while the self curing resin hardens.

Referring to FIG. 6, there is shown the bonder tip member 114 of the present invention. It will be appreciated that although a straight cylindrical shaped body 124 of the bonder tip member 114 is preferred and shown, it is also within the spirit and scope of the present invention to have a shape generally similar to FIGS. 1 through 4. The distal section 130 of the body 124 may be made with a diameter greater than the diameter of the proximal section 126, where an edge may be formed so that when the bonder tip member 114 is press fitted within the opening at the proximal end of the tool member, the edge rests on the rim of the proximal end (see FIG. 2).

Figure 9:
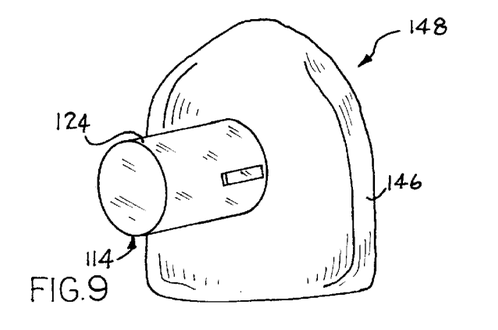
FIG. 9 is an illustration of the present invention disposable applicator, showing the disposable applicator abutting against the surface of a tooth without a dental tool member holding the bonder tip member.

Referring to FIG. 9, there is depicted an illustration of the cylindrical or ovoid shaped body 124 of the translucent bonder tip member 114 positioned against the surface 146 of the tooth 148, thereby forming a custom orthodontic bracket 147 (see FIG. 10) which is bonded to the surface 146 of the tooth 148.

Figure 10:
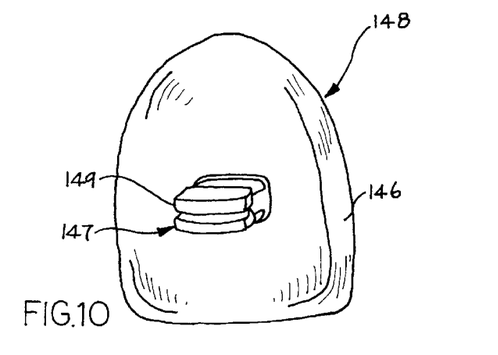
FIG. 10 is an illustration of the orthodontic bracket formed by the present invention disposable applicator.

Referring to FIG. 10, there is depicted an illustration of the custom orthodontic bracket 147 which is formed by the translucent bonder tip member 114. The orthodontic bracket 147 has a slot 149 which is formed by the raised ridge 135 so that an orthodontic wire may be placed therein to correct irregular teeth of a patient. The orthodontic bracket 147 is the positive shape of the rectangular shaped contour cavity 140. Essentially the technique is to have the disposable applicator that assists the orthodontist to form the orthodontic bracket 147 to the back or front surfaces 146 of the tooth 148 for retaining an orthodontic wire during or after orthodontic treatment. The unique feature of the disposable applicator is that it consistently forms a custom orthodontic bracket every time.

The process requires that first the bonder tip member 114 be held by a dental tool (shown in FIGS. 1 and 2) or by any suitable means such as a dental forceps tool. Then the distal end 132 of the cylindrical shaped body 124 is positioned against the surface 146 of the tooth 148 and then the curing light is shined on the resin through the translucent bonder tip member 114 so that the resin becomes hardened. Thereafter the cylindrical shaped body 124 is removed from its position against the tooth, and thereby a custom orthodontic bracket 147 is formed on the surface 146 of the tooth 148, where an orthodontic wire may be placed thereon and held in position to correct irregular teeth of a patient.

The cylindrical shaped body 124 of the bonder tip member 114 can be made from several materials. The manufacturing process which could accommodate the construction of the bonder tip member 114 can be injection, etc. or other molding process. By way of example, the cylindrical shaped body 124 can be made of synthetic rubber or other suitable material. The present invention conforms to conventional forms of manufacture or any other conventional way known to one skilled in the art.

In addition, the cylindrical shaped body 124 may be transparent so that a curing light can shine on the resin through the cylindrical shaped body 124 of the bonder tip member 114 to harden the resin or the cylindrical shaped body 124 may not be transparent, and thereby a self curing resin is utilized that does not require a curing light.

Referring to FIGS. 11 through 15, there is shown still another embodiment of the present invention disposable applicator. The disposable applicator comprises an elongated dental tool member which is identical to the one shown in FIG. 2 (therefore the description of the dental tool member will not be repeated), and a translucent bonder tip member 214. The translucent bonder tip member 214 is installed in the dental tool member exactly the same as shown in FIGS. 1 and 2.

Figure 11:
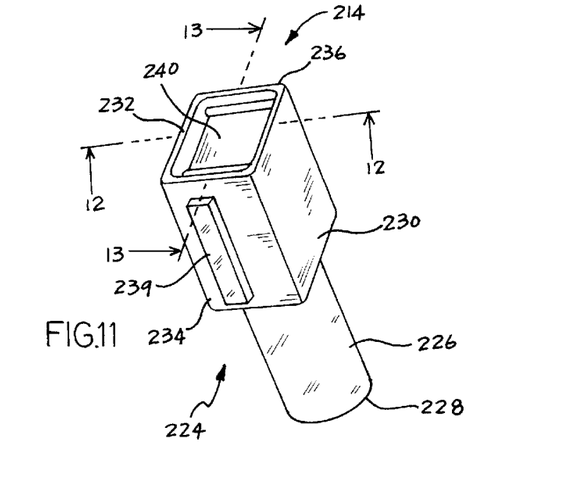
FIG. 11 is a perspective view of still another embodiment of the present invention disposable applicator for forming a small custom orthodontic button and retaining a conventional orthodontic button to surfaces of teeth so that a rubber band may be wrapped around the button for adjusting the teeth.
Figure 14:
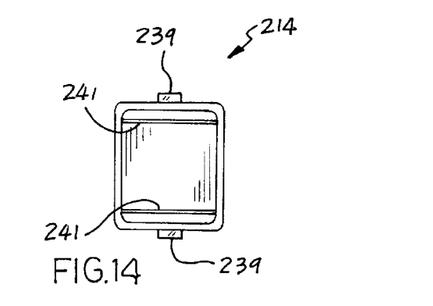
FIG. 14 is a top plan view of the present invention shown in FIG. 11.

Referring to FIGS. 11 and 14, there are shown at 214 respective perspective and top plan views of the translucent bonder tip member of the present invention. The bonder tip member 214 is utilized for forming a custom orthodontic button to surfaces of teeth (see FIG. 16). The bonder tip member 214 has a generally cylindrical or ovoid or rectangular shaped body 224 which has a proximal section 226 with a proximal end 228 and a distal section 230 with a distal end 232. The proximal section 226 is generally a cylindrical shape while the distal section 230 is generally a rectangular shape. The distal end 232 of the bonder tip member 214 has a periphery rim 236 and a receptacle or rectangular shaped contour cavity 240 therein surrounded by the periphery rim 236.

Figure 12:
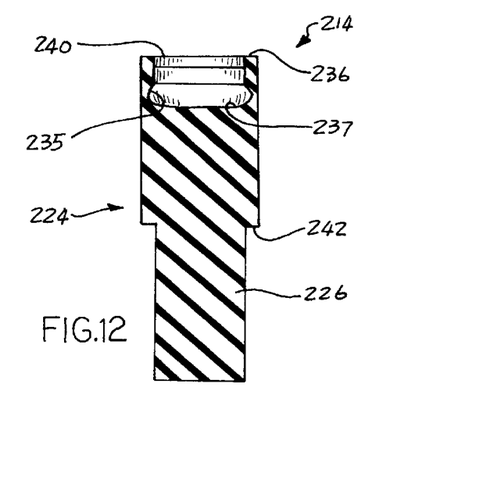
FIG. 12 is a cross-sectional view taken along line 12—12 of FIG. 11.
Figure 13:
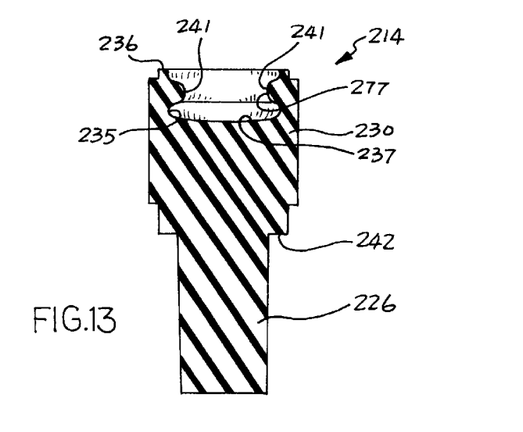
FIG. 13 is a cross-sectional view taken along line 13—13 of FIG. 11.

Referring to FIGS. 12 and 13, there are shown respective cross-sectional views of the bonder tip member 214. The cavity 240 has a widened portion 235 near the bottom 237 of the cavity 240 and a narrow portion 241 located at a midsection 271 of the cavity 240. By way of example, the shaped contour cavity 240 has a depth of $100/1000$ of an inch. It will be appreciated that the dimensions described above are merely one illustrative embodiment and can include many other comparable sets of dimensions.

The bonder tip member 214 also has one or two guide members or ribs 239 running in a partial length of the body 224 on either side and located on the distal section 230. The guide members 239 provide a visual aid for the orthodontist to configure the bonder tip member 214 to form the orthodontic button.

It will be appreciated that the shaped contour cavity 240 is not limited to the structure just described above. It is emphasized that while the rectangular shaped contour cavity 240 is preferred, it is also within the spirit and scope of the present invention to have a multiplicity of shaped contour cavities, for example, a negative-mold shape which is similar to an anvil, a flat head portion of a screw or any other suitable shapes. In addition, it will not be too difficult for one skilled in the art to have a different shape negative-mold structure created by the bonder tip member 214.

The bonder tip member 214 is a tiny translucent device such that the curing light can shine on the resin through the translucent body 224 so that the resin becomes hardened and forms a small custom orthodontic button to the surfaces of the teeth. Alternatively, it is not necessary that the type of curing resin utilized be resin that requires a curing light. It is also possible to utilize self curing resin which simply can be held in place during the hardening process. When using self curing resin, the bonded tip member 214 does not have to be translucent since it is not required to have any curing light shine through it. Through use of the self curing resin, the process is the same as just described except that no curing light is required and the bonder tip member 214 is simply held in position while the self curing resin hardens.

Referring to FIG. 12, there is shown the bonder tip member 214 of the present invention. From this view, the distal section 230 of the body 224 is greater than the proximal section 226, where an edge 242 is formed so that when the bonder tip member 214 is press fitted within the opening at the proximal end of the tool member, the edge 242 rests on the rim of the proximal end (see FIG. 2).

Figure 15:
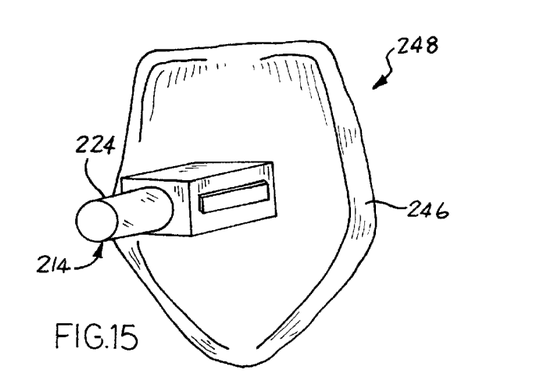
FIG. 15 is an illustration of the present invention disposable applicator, showing the disposable applicator abutting against the surface of a tooth without a dental tool member holding the bonder tip member.

Referring to FIG. 15, there is depicted an illustration of the cylindrical or ovoid shaped body 224 of the translucent bonder tip member 214 positioned against the surface 246 of the tooth 248, thereby forming a custom orthodontic button 247 (see FIG. 16) which is bonded to the surface 246 of the tooth 248.

Figure 16:
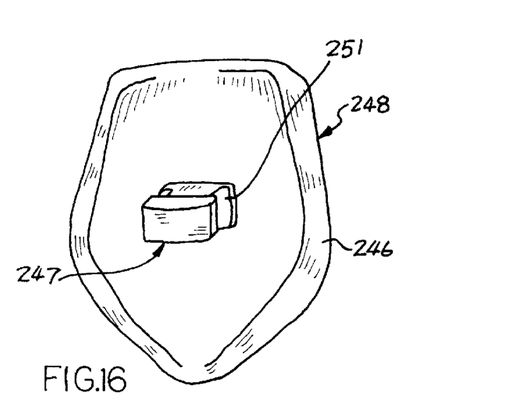
FIG. 16 is an illustration of the orthodontic button formed by the present invention disposable applicator.

Referring to FIG. 16, there is depicted an illustration of the custom orthodontic button 247 which is formed by the translucent bonder tip member 214. The orthodontic button 247 has two opposite grooves 251 for holding a rubber band around the button in order to adjust the teeth. The orthodontic button 247 is the positive shape of the rectangular shaped contour cavity 240, and the grooves 251 of the button 247 are formed by the narrow portion 241 of the cavity 240 in the member 214. Essentially the technique is to have the disposable applicator that assists the orthodontist to form the orthodontic button 247 to the back or front surfaces 246 of the tooth 248 for retaining the rubber band during or after orthodontic treatment. The unique feature of the disposable applicator is that it consistently forms a custom orthodontic button every time.

The process requires that first the bonder tip member 214 be held by a dental tool (shown in FIGS. 1 and 2) or by any suitable means such as a dental forceps tool. Then the distal end 232 of the cylindrical shaped body 224 is positioned against the surface 246 of the tooth 248 and then the curing light is shined on the resin through the translucent bonder tip member 214 so that the resin becomes hardened. Thereafter the cylindrical shaped body 224 is removed from its position against the tooth, and thereby an orthodontic button 247 is formed on the surface 246 of the tooth 248, where an rubber band may be placed thereon and held in position to correct irregular teeth of a patient.

The body 224 of the bonder tip member 214 can be made from several materials. The manufacturing process which could accommodate the construction of the bonder tip member 214 can be injection, etc. or other molding process. By way of example, the body 224 can be made of synthetic rubber or other suitable material. The present invention conforms to conventional forms of manufacture or any other conventional way known to one skilled in the art. In addition, the body 224 may be transparent so that a curing light can shine on the resin through the body 224 of the bonder tip member 214 to harden the resin or the cylindrical shaped body 224 may not be transparent, and thereby a self curing resin is utilized that does not require a curing light.

The bonder tip member 214 may be designed to accommodate existing orthodontic buttons. The shaped contour cavity will be a predetermined shape, which snugly retains a conventional orthodontic button therein so that an orthodontist can rapidly and effortlessly hold the orthodontic button to bond it to the surface of each tooth.

Defined broadly, the present invention is a disposable applicator for forming an orthodontic bracket to surfaces of teeth, comprising: (a) a body having a distal section with a distal end and a proximal section with a proximal end, the distal end having a periphery rim and a shaped contour cavity, where the periphery rim surrounds the shaped contour cavity; (b) a raised ridge integrally formed on a bottom of said shaped contour cavity and extending upwardly and below said periphery rim of said body; (c) a narrow portion located at a midsection of said shaped contour cavity for forming at least one groove on the orthodontic bracket and perpendicular to said raised ridge; (d) a tool member having a distal end and a proximal end with an opening therein; and (e) said proximal section of said body installed into said opening at said proximal end of said tool member; (f) whereby said shaped contour cavity is filled with curing resin and said periphery rim is placed against each respective surface of said teeth to hold the curing resin thereon until the curing resin becomes hardened, thereby forming the orthodontic bracket with a wire slot thereon.

Defined in detail, the present invention is a disposable applicator for forming an orthodontic bracket to surfaces of teeth, comprising: (a) a body having a distal section with a distal end and a proximal section with a proximal end, the diameter of the distal section being greater than the diameter of the proximal section, the distal end having a periphery rim and a shaped contour cavity, where the periphery rim surrounds the shaped contour cavity; (b) a raised ridge integrally formed on a bottom of said shaped contour cavity and extending upwardly and below said periphery rim of said body; (c) a narrow portion located at a midsection of said shaped contour cavity for forming at least one groove on the orthodontic bracket and perpendicular to said raised ridge; (d) a tool member having a distal end and a proximal end with an opening therein; and (e) said proximal section of said body installed into said opening at said proximal end of said tool member; (f) whereby said shaped contour cavity is filled with curing resin and said periphery rim is placed against each respective surface of said teeth to hold the curing resin thereon until the curing resin becomes hardened, thereby forming the orthodontic bracket with a wire slot thereon.

Defined alternatively broadly, the present invention is a disposable applicator for forming an orthodontic button to surfaces of teeth, comprising: (a) a body having a distal section with a distal end and a proximal section with a proximal end, the distal end having a periphery rim and a shaped contour cavity, where the periphery rim surrounds the shaped contour cavity; (b) a narrow portion located at a midsection of said shaped contour cavity for forming at least one groove on the orthodontic button; (c) a tool member having a distal end and a proximal end with an opening therein; and (d) said proximal section of said body installed into said opening at said proximal end of said tool member; (e) whereby said shaped contour cavity is filled with curing resin and said periphery rim is placed against each respective surface of said teeth to hold the curing resin thereon until the curing resin becomes hardened, thereby forming the orthodontic button with the at least one groove for a rubber band to wrap around the at least one groove.

Defined alternatively in detail, the present invention is a disposable applicator for forming an orthodontic button to surfaces of teeth, comprising: (a) a body having a distal section with a distal end and a proximal section with a proximal end, the distal section of the body being larger than the proximal section, the distal end having a periphery rim and a shaped contour cavity, where the periphery rim surrounds the shaped contour cavity; (b) a narrow portion located at a midsection of said shaped contour cavity for forming at least one groove on the orthodontic button; (c) a tool member having a distal end and a proximal end with an opening therein; and (d) said proximal section of said body installed into said opening at said proximal end of said tool member; (e) whereby said shaped contour cavity is filled with curing resin and said periphery rim is placed against each respective surface of said teeth to hold the curing resin thereon until the curing resin becomes hardened, thereby forming the orthodontic button with the at least one groove for a rubber band to wrap around the at least one groove.

Defined more broadly, the present invention is an applicator for forming an orthodontic attachment to surfaces of teeth, comprising: (a) a body having a distal end and a proximal end, the distal end having a periphery rim and a shaped cavity for accommodating curing resin therein to form the orthodontic attachment, where the periphery rim surrounds the shaped cavity; (b) whereby said shaped cavity of said body is filled with curing resin and said periphery rim is positioned against a surface of a tooth to hold the curing resin thereon until the curing resin becomes hardened, thereby forming the orthodontic attachment thereon.

Alternatively defined, the present invention is an applicator for retaining a conventional orthodontic button to surfaces of teeth, comprising: (a) a body having a distal end and a proximal end, the distal end having a predetermined shaped cavity therein, where the predetermined shaped cavity snugly retains the conventional button therein to be bonded to the surfaces of a tooth; (b) whereby said predetermined shaped cavity of said body retains the conventional orthodontic button therein and positions the conventional orthodontic button against the surface of the tooth to be bonded, thereby applying curing resin to a surface of the conventional orthodontic button to be bonded to the surface of the tooth.

Also alternatively defined, the present invention is a method for forming an orthodontic attachment to a surface of a tooth, comprising the steps of: (a) providing a body having a receptacle means therein; (b) filling said receptacle means of said body with curing resin; (c) placing said body on the surface of the tooth and waiting for the curing resin to become hardened and bonded to the tooth; (d) removing said body so that the orthodontic attachment is formed on the surface of the tooth; and (e) repeating steps (b) through (d) for each tooth which requires the orthodontic attachment.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modifications in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. A disposable applicator for forming an orthodontic bracket to surfaces of teeth, comprising:
    a. a body having a distal section with a distal end and a proximal section with a proximal end, the distal end having a periphery rim and a shaped contour cavity, where the periphery rim surrounds the shaped contour cavity;
    b. a raised ridge integrally formed on a bottom of said shaped contour cavity and extending upwardly and below said periphery rim of said body;
    c. a narrow portion located at a midsection of said shaped contour cavity for forming at least one groove on the orthodontic bracket and perpendicular to said raised ridge;
    d. a tool member having a distal end and a proximal end with an opening therein; and
    e. said proximal section of said body installed into said opening at said proximal end of said tool member;
    f. whereby said shaped contour cavity is filled with curing resin and said periphery rim is placed against each respective surface of said teeth to hold the curing resin thereon until the curing resin becomes hardened, thereby forming the orthodontic bracket with a wire slot thereon.

2. The disposable applicator in accordance with claim 1 further comprising two oppositely disposed guide members located on said distal section of said body and running in line with said raised ridge for assisting in configuring said orthodontic bracket.

3. The disposable applicator in accordance with claim 1 wherein the diameter of said distal section of said body is greater than the diameter of said proximal section.

4. The disposable applicator in accordance with claim 1 wherein said body is translucent.

5. The disposable applicator in accordance with claim 1 wherein said tool member is forceps.

6. The disposable applicator in accordance with claim 1 wherein said body is made of rubber material.

7. The disposable applicator in accordance with claim 1 wherein said shaped contour cavity is generally rectangular.

8. A disposable applicator for forming an orthodontic bracket to surfaces of teeth, comprising:
    a. a body having a distal section with a distal end and a proximal section with a proximal end, the diameter of the distal section being greater than the diameter of the proximal section, the distal end having a periphery rim and a shaped contour cavity, where the periphery rim surrounds the shaped contour cavity;
    b. a raised ridge integrally formed on a bottom of said shaped contour cavity and extending upwardly and below said periphery rim of said body;
    c. a narrow portion located at a midsection of said shaped contour cavity for forming at least one groove on the orthodontic bracket and perpendicular to said raised ridge;
    d. a tool member having a distal end and a proximal end with an opening therein; and
    e. said proximal section of said body installed into said opening at said proximal end of said tool member;
    f. whereby said shaped contour cavity is filled with curing resin and said periphery rim is placed against each respective surface of said teeth to hold the curing resin thereon until the curing resin becomes hardened, thereby forming the orthodontic bracket with a wire slot thereon.

9. A disposable applicator for forming an orthodontic button to surfaces of teeth, comprising:
    a. a body having a distal section with a distal end and a proximal section with a proximal end, the distal end having a periphery rim and a shaped contour cavity, where the periphery rim surrounds the shaped contour cavity;
    b. a narrow portion located at a midsection of said shaped contour cavity for forming at least one groove on the orthodontic button;
    c. a tool member having a distal end and a proximal end with an opening therein; and
    d. said proximal section of said body installed into said opening at said proximal end of said tool member;
    e. whereby said shaped contour cavity is filled with curing resin and said periphery rim is placed against each respective surface of said teeth to hold the curing resin thereon until the curing resin becomes hardened, thereby forming the orthodontic button with the at least one groove for a rubber band to wrap around the at least one groove.

10. The disposable applicator in accordance with claim 9 further comprising two oppositely disposed guide members located on said distal section of said body for assisting in configuring the orthodontic button.

11. The disposable applicator in accordance with claim 9 wherein said distal section of said body is larger than said proximal section.

12. The disposable applicator in accordance with claim 9 wherein said body is made of rubber material.

13. The disposable applicator in accordance with claim 9 wherein said body is translucent.

14. The disposable applicator in accordance with claim 9 wherein said tool member is forceps.

15. The disposable applicator in accordance with claim 9 wherein said shaped contour cavity is generally rectangular.

16. A disposable applicator for forming an orthodontic button to surfaces of teeth, comprising:
    a. a body having a distal section with a distal end and a proximal section with a proximal end, the distal section of the body being larger than the proximal section, the distal end having a periphery rim and a shaped contour cavity, where the periphery rim surrounds the shaped contour cavity;
    b. a narrow portion located at a midsection of said shaped contour cavity for forming at least one groove on the orthodontic button;
    c. a tool member having a distal end and a proximal end with an opening therein; and
    d. said proximal section of said body installed into said opening at said proximal end of said tool member;
    e. whereby said shaped contour cavity is filled with curing resin and said periphery rim is placed against each respective surface of said teeth to hold the curing resin thereon until the curing resin becomes hardened, thereby forming the orthodontic button with the at least one groove for a rubber band to wrap around the at least one groove.

17. An applicator for forming an orthodontic attachment to surfaces of teeth, comprising:

a. a body having a distal end and a proximal end, the distal end having a periphery rim and a shaped cavity for accommodating curing resin therein to form the orthodontic attachment, where the periphery rim surrounds the shaped cavity; and b. a raised ridge formed on a bottom of said shaped cavity, whereby when the orthodontic attachment is formed, the raised ridge forms a slot for accommodating an orthodontic wire;

c. whereby said shaped cavity of said body is filled with curing resin and said periphery rim is positioned against a surface of a tooth to hold the curing resin thereon until the curing resin becomes hardened, thereby forming the orthodontic attachment thereon.

18. The applicator in accordance with claim 17 further comprising at least one guide member located on said body and adjacent to said distal end for assisting in configuring the orthodontic attachment.

19. The applicator in accordance with claim 17 further comprising a tool means for holding said body.

20. The applicator in accordance with claim 19 wherein said tool means is a forceps.

21. The applicator in accordance with claim 17 further comprising a narrow portion located at a midsection of said shaped cavity, whereby when the orthodontic attachment is formed, the narrow portion forms at least one groove for accommodating an orthodontic rubber band.

22. The applicator in accordance with claim 17 wherein said shaped cavity is generally rectangular.

23. An applicator for retaining a conventional orthodontic button to surfaces of teeth, comprising:

a. a body having a distal end and a proximal end, the distal end having a predetermined shaped cavity therein, where the predetermined shaped cavity snugly retains the conventional button therein to be bonded to the surfaces of a tooth; and b. a narrow portion located at a midsection of said shaped cavity for accommodating an orthodontic elastomeric ligature;

c. whereby said predetermined shaped cavity of said body retains the conventional orthodontic button therein and positions the conventional orthodontic button against the surface of the tooth to be bonded, thereby applying curing resin to a surface of the conventional orthodontic button to be bonded to the surface of the tooth.

24. The applicator in accordance with claim 23 further comprising a tool means for holding said body.

25. The applicator in accordance with claim 24 wherein said tool means is forceps.

26. A method for forming an orthodontic attachment to a surface of a tooth, comprising the steps of:

a. providing a body having a receptacle means therein;

b. filling said receptacle means of said body with curing resin;

c. placing said body on the surface of the tooth and waiting for the curing resin to become hardened and bonded to the tooth;

d. removing said body so that the orthodontic attachment is formed on the surface of the tooth; and e. repeating steps (b) through (d) for each tooth which requires the orthodontic attachment.

27. The method in accordance with claim 26 further comprising the step of providing a tool means for retaining said body.

28. An applicator for forming an orthodontic attachment to surfaces of teeth, comprising:

a. a body having a distal end and a proximal end, the distal end having a periphery rim and a shaped cavity for accommodating curing resin therein to form the orthodontic attachment, where the periphery rim surrounds the shaped cavity; and b. a narrow portion located at a midsection of said shaped cavity, whereby when the orthodontic attachment is formed, the narrow portion forms at least one groove for accommodating an orthodontic elastomeric ligature;

c. whereby said shaped cavity of said body is filled with curing resin and said periphery rim is positioned against a surface of a tooth to hold the curing resin thereon until the curing resin becomes hardened, thereby forming the orthodontic attachment thereon.

29. The applicator in accordance with claim 28 further comprising at least one guide member located on said body and adjacent to said distal end for assisting in configuring the orthodontic attachment.

30. The applicator in accordance with claim 28 further comprising a tool means for holding said body.

31. The applicator in accordance with claim 30 wherein said tool means is a forceps.

32. The applicator in accordance with claim 28 further comprising a raised ridge formed on a bottom of said shaped cavity, whereby when the orthodontic attachment is formed, the raised ridge forms a slot for accommodating an orthodontic wire.

33. The applicator in accordance with claim 28 wherein said shaped cavity is generally rectangular.

\* \* \* \* \*